US010631760B2

(12) United States Patent
Dracup et al.

(10) Patent No.: US 10,631,760 B2
(45) Date of Patent: Apr. 28, 2020

(54) METHOD FOR PREDICTION, DETECTION, MONITORING, ANALYSIS AND ALERTING OF SEIZURES AND OTHER POTENTIALLY INJURIOUS OR LIFE-THREATENING STATES

(76) Inventors: Jeffrey Albert Dracup, San Diego, CA (US); Alexander Patterson Dracup, San Diego, CA (US); Steven Barkolas, Poway, CA (US)

(*) Notice: Subject to any disclaimer, the term of this patent is extended or adjusted under 35 U.S.C. 154(b) by 776 days.

(21) Appl. No.: 13/602,053

(22) Filed: Aug. 31, 2012

(65) Prior Publication Data

US 2013/0060167 A1 Mar. 7, 2013

Related U.S. Application Data

(60) Provisional application No. 61/530,928, filed on Sep. 2, 2011.

(51) Int. Cl.
| | |
|---|---|
| *A61B 5/00* | (2006.01) |
| *A61B 5/11* | (2006.01) |
| *G08B 21/04* | (2006.01) |
| *G16H 50/20* | (2018.01) |
| *G16H 50/70* | (2018.01) |
| *G16H 80/00* | (2018.01) |
| *A61B 5/024* | (2006.01) |
| *A61B 5/053* | (2006.01) |

(Continued)

(52) U.S. Cl.
CPC .............. *A61B 5/11* (2013.01); *A61B 5/0022* (2013.01); *A61B 5/4094* (2013.01); *G08B 21/0446* (2013.01); *G08B 21/0453* (2013.01); *G16H 50/20* (2018.01); *G16H 50/70* (2018.01); *G16H 80/00* (2018.01); *A61B 5/02055* (2013.01); *A61B 5/02405* (2013.01); *A61B 5/0488* (2013.01); *A61B 5/0531* (2013.01); *A61B 5/1117* (2013.01); *A61B 2560/045* (2013.01); *A61B 2562/0219* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,995,868 A | * | 11/1999 | Dorfmeister et al. | ........ 600/544 |
| 6,594,524 B2 | * | 7/2003 | Esteller | ................ A61B 5/0482 |
| | | | | 600/544 |

(Continued)

FOREIGN PATENT DOCUMENTS

WO    WO 2011149565 A1 * 12/2011 ............... A61B 5/01

*Primary Examiner* — Niketa I Patel
*Assistant Examiner* — Shirley X Jian

(57) ABSTRACT

The present invention provides a method for predicting seizures and for detecting seizures, and other potentially injurious or life-threatening events, optionally in conjunction with a mobile device. In an embodiment, a portable device provides epilepsy seizure prediction, detection, monitoring, analysis and alerting for epilepsy patients or other people afflicted with seizures. In an embodiment, the portable device may alert and communicate information to health care providers, caregivers and family members, emergency services, and the like. Collected data may be reviewed and analyzed for use in developing specific criteria for predicting and detecting seizures and other potentially injurious or life-threatening events.

14 Claims, 5 Drawing Sheets

(51) Int. Cl.
*A61B 5/0205* (2006.01)
*A61B 5/0488* (2006.01)

(56) References Cited

U.S. PATENT DOCUMENTS

| | | | | |
|---|---|---|---|---|
| 7,558,622 | B2* | 7/2009 | Tran | A61B 5/0022 600/509 |
| 7,733,224 | B2* | 6/2010 | Tran | G06F 19/3418 340/3.1 |
| 8,140,143 | B2* | 3/2012 | Picard | A61B 5/0531 600/382 |
| 8,655,441 | B2* | 2/2014 | Fletcher | A61B 5/0002 600/382 |
| 8,795,173 | B2* | 8/2014 | Poh | A61B 5/02405 600/301 |
| 9,254,383 | B2* | 2/2016 | Simon | A61N 1/36021 |
| 9,339,195 | B2* | 5/2016 | Pitruzzello | A61B 5/01 |
| 2003/0144829 | A1* | 7/2003 | Geatz | G06F 19/322 703/22 |
| 2005/0115561 | A1* | 6/2005 | Stahmann et al. | 128/200.24 |
| 2006/0235489 | A1* | 10/2006 | Drew | A61B 5/0006 607/60 |
| 2007/0139183 | A1* | 6/2007 | Kates | G08B 25/005 340/521 |
| 2007/0213785 | A1* | 9/2007 | Osorio | A61B 5/4094 607/45 |
| 2007/0276270 | A1* | 11/2007 | Tran | A61B 5/0022 600/508 |
| 2008/0001735 | A1* | 1/2008 | Tran | G06F 19/3418 340/539.22 |
| 2008/0004904 | A1* | 1/2008 | Tran | A61B 5/0006 705/2 |
| 2008/0033508 | A1* | 2/2008 | Frei et al. | 607/62 |
| 2008/0139899 | A1* | 6/2008 | Student et al. | 600/301 |
| 2008/0195166 | A1* | 8/2008 | Sun et al. | 607/18 |
| 2008/0208074 | A1* | 8/2008 | Snyder et al. | 600/545 |
| 2009/0124870 | A1* | 5/2009 | Arends | A61B 5/02438 600/301 |
| 2009/0137921 | A1* | 5/2009 | Kramer | A61B 5/1118 600/544 |
| 2009/0312998 | A1* | 12/2009 | Berckmans | G06F 19/3437 703/11 |
| 2010/0268056 | A1* | 10/2010 | Picard | A61B 5/0531 600/388 |
| 2010/0280334 | A1* | 11/2010 | Carlson | A61N 1/36082 600/301 |
| 2010/0280335 | A1* | 11/2010 | Carlson | A61N 1/36082 600/301 |
| 2010/0280336 | A1* | 11/2010 | Giftakis | A61B 5/0476 600/301 |
| 2010/0280574 | A1* | 11/2010 | Carlson | A61N 1/36082 607/59 |
| 2010/0280579 | A1* | 11/2010 | Denison | A61N 1/36082 607/62 |
| 2010/0292602 | A1* | 11/2010 | Worrell et al. | 600/544 |
| 2011/0004072 | A1* | 1/2011 | Fletcher | A61B 5/0002 600/300 |
| 2011/0092780 | A1* | 4/2011 | Zhang | A61B 5/053 600/301 |
| 2011/0137371 | A1* | 6/2011 | Giftakis | A61N 1/36139 607/45 |
| 2011/0245629 | A1* | 10/2011 | Giftakis | A61B 5/0476 600/301 |
| 2011/0270095 | A1* | 11/2011 | Bukhman | 600/483 |
| 2011/0270347 | A1* | 11/2011 | Frei et al. | 607/45 |
| 2011/0294429 | A1* | 12/2011 | Shirakata et al. | 455/41.2 |
| 2012/0296175 | A1* | 11/2012 | Poh | A61B 5/02405 600/301 |
| 2013/0079602 | A1* | 3/2013 | Picard | A61B 5/0022 600/301 |
| 2013/0080185 | A1* | 3/2013 | Picard | A61B 5/0022 705/2 |
| 2013/0096840 | A1* | 4/2013 | Osorio | A61B 5/02055 702/19 |
| 2013/0116514 | A1* | 5/2013 | Kroner | A61B 7/00 600/301 |
| 2013/0218053 | A1* | 8/2013 | Kaiser et al. | 600/595 |
| 2014/0081090 | A1* | 3/2014 | Picard | G06F 19/3418 600/301 |
| 2016/0151628 | A1* | 6/2016 | Simon | A61N 1/36021 607/2 |

\* cited by examiner

METHOD FOR PREDICTION, DETECTION, MONITORING, ANALYSIS AND ALERTING OF SEIZURES AND OTHER POTENTIALLY INJURIOUS OR LIFE-THREATENING STATES

CROSS-REFERENCE TO RELATED APPLICATION

The application claims priority from U.S. Provisional Patent Application No. 61/530,928, filed on Sep. 2, 2011, the contents of which are incorporated herein by reference.

BACKGROUND OF THE INVENTION

The subject matter discussed in this background section should not be assumed to be prior art merely as a result of its mention herein. A problem mentioned in this background section or associated with the subject matter of this background section should not be assumed to have been recognized in the prior art. The subject matter in this background section at the most represents different approaches, which in and of themselves may also be inventions.

Over two million people in the United States suffer from epileptic seizures. During a seizure the patient usually is unable to get help, talk, think, or act. In some instances it is very important for doctors and caregivers to be able to detect seizures and give the patient immediate help. Patients may suffer related injuries, such as from falls, traffic accidents, and other events. There are some types of seizures, if not attended to, that can be fatal.

Health care providers need condensed and specific information on patients to provide improved treatment. Specifically, when muscular activity and skin perspiration may shed light on patient status, continuous monitoring may be useful. Continuous monitoring may be indicated due to certain patterns in a patient's status, seizure history, or other medical conditions. Seizures may involve motor convulsions. Certain characteristics may be associated prior to a seizure, such as surface muscular contractions and increased skin perspiration, sometimes at specific locations.

With increased focus on financial management of health care there exists a need for monitoring patients in institutions or at home and in everyday environments to effectively and properly diagnose and treat a patient.

Currently there are no home or personal seizure monitoring or detecting devices used widely in the public. There are Electroencephalography (EEG) machines, which measure electrical neurological activity. However, EEGs are for hospital use and the hardware is large and expensive. The EEGs may analyze brainwaves to detect the onset or the occurrence of a seizure. EEGs require probes to be mounted on the patients' scalp to sense, extract, and transmit data. The probes are uncomfortable, intrusive, and awkward. The probes and associated equipment restricts patients' movements and may cause scarring. EEG can only detect activity in the cortex, the outer portion of the brain. If a seizure begins in the amygdala, the EEG will not be able to detect the seizure, but skin sensors can detect the same seizure. Also, the graphs from the EEGs need to be reviewed and interpreted manually by trained personnel, such as nurses and medical assistants.

Portable devices are increasingly used for multiple tasks that range from telephony to video to computing to audio and other entertainment and instructional uses. Portable devices may be used to facilitate communication, including via a communication service. Such devices may include mobile telephones, personal digital assistants (PDAs), portable video/music players, electronic books, electronic book readers, tablet computers, portable gaming devices, and the like. Some of such devices include the iPad (trademarked by Apple, Inc.), the iPod (trademarked by Apple, Inc.), the iPhone (trademarked by Apple, Inc.), the BlackBerry (trademarked by RIM, Inc.), devices based on the Android (trademarked by Google, Inc.) operating system, such as the Nexus 7 tablet (trademarked by Google, Inc.), and other portable devices.

It would be advantageous to provide a communications service that would include one or more of the features of 1) detecting (or establishing or allowing entry of) a user's location; 2) assigning identifying information to the user (or allowing identifying information to be entered by a user); 3) assigning identifying information to other users (or allowing users to enter identifying information); 4) filtering the transmitted identifying information according to attributes selected by the located user; and 5) initiating an electronic conversation between the located user and at least one of the other users selected by the located user.

It would be advantageous to provide a method and apparatus for detecting seizures and other abnormal motor activity that may include one or more of the features of 1) sensing movement using a reference sensor having at least one conductive pad arranged to be placed on the skin of a body at a reference location for sensing, over a prolonged period of time, reference Surface Electromyography (s-emg) signals and/or electrodermal activity at the reference location; 2) placing at least one monitoring sensor having at least one conductive pad arranged to be placed on the skin of a respective limb of the body at a monitoring location for sensing, over said prolonged period of time, monitoring Surface Electromyography (s-emg) signals and/or electrodermal activity at the monitoring location; 3) comparing said reference signals with said monitoring signals; 4) producing an output by comparison of said reference signals and said monitoring signals; 5) detecting movement via an accelerometer, gyroscope, and/or other equipment; 6) genetic algorithm or other suitable method continuously analyzing data stored and coming from each user, and periodically optimizing the seizure/abnormal movement algorithm for each particular user for a detection and alerting algorithm for that user; and 7) using equipment that is discreet, comfortable, and convenient, such as in cooperation with a mobile device or other suitable method continuously analyzing data stored and coming from each user, and periodically optimizing the seizure/abnormal movement algorithm for each particular user for a detection and alerting algorithm for that user.

SUMMARY OF THE INVENTION

In one aspect of the present invention, a portable device comprises an attachment apparatus for attaching a portable device to a person, an input system for inputting detected parameters for a specific type of motion by the person, an accelerometer and/or gyroscope unit for measuring motion data, a memory unit for storing settings for detecting the specific type of motion by the person, an algorithm for analyzing the measured motion data, comparing characteristics of the specific type of motion by the person to the measured motion data, and determining whether an alert should be sent based on the comparing, a processor to implement the algorithm and generate an indication that a specific abnormal motion may have occurred based on the algorithm, wherein the abnormal motion includes a seizure, a housing for enclosing the memory unit and the processor, a monitoring sensor having at least one conductive pad arranged to be placed on a respective limb of the body of the person at a monitoring location for sensing and monitoring, over a prolonged period of time, signals at the monitoring location, and a display attached to the housing in a manner for settings so that the specific abnormal motion or a status may be viewed, wherein the input system is attached to the housing in a manner so that the person or another person may enter settings for the specific type of abnormal motion. In other embodiments, the portable device may not be attached to a patient or user.

In another aspect of the present invention, a system comprises a motion detector measuring motion data associated with a user, an input system for inputting parameters for a specific type of motion by the user, a memory unit for storage of an algorithm including analyzing motion data, determining whether motion data relating to a specific type of motion has occurred based on the analyzing of motion data, and if it is determined that the specific type of motion has occurred, generating an alert that the specific type of motion occurred, based on the determining, a processor for implementing the algorithm to determine whether the motion data retrieved by the motion detector corresponds to the specific type of motion, wherein the specific type of motion is an abnormal motion, including a seizure, an output system for providing values of current settings and/or feedback regarding implementation of settings, and an advice system to provide general instructions for care of a seizure victim and specific instructions for care of the user based on the motion data associated with the user.

In a further aspect of the present invention, a method for abnormal motion detection, comprises downloading an optimal available abnormal motion detection algorithm to a mobile device, updating the mobile device with the optimal available abnormal motion detection algorithm, periodically activating device sensors in listening mode, keeping device sensors active in the event that abnormal motion characteristic patterns are detected detecting whether abnormal motion characteristic patterns occur, recording sensor data, uploading sensor data, prompting a user to affirm an occurrence of a seizure, alerting the user of an alarm sequence, activating an alarm sequence in the event of no user response or of affirmation of seizure by the user, transmitting a device-initiated alarm to a monitoring station, transmitting an alert to pre-designated alert recipients, recording seizure details, and transmitting seizure details to the monitoring station.

These and other aspects, objects, features and advantages of the present invention, are specifically set forth in, or will become apparent from, the following detailed description of an exemplary embodiment of the invention.

BRIEF DESCRIPTION OF THE DRAWINGS

The above and other aspects of the present invention will become more apparent by the following detailed description of exemplary embodiments thereof with reference to the attached drawings, in which.

DETAILED DESCRIPTION OF THE INVENTION

Figure 1:
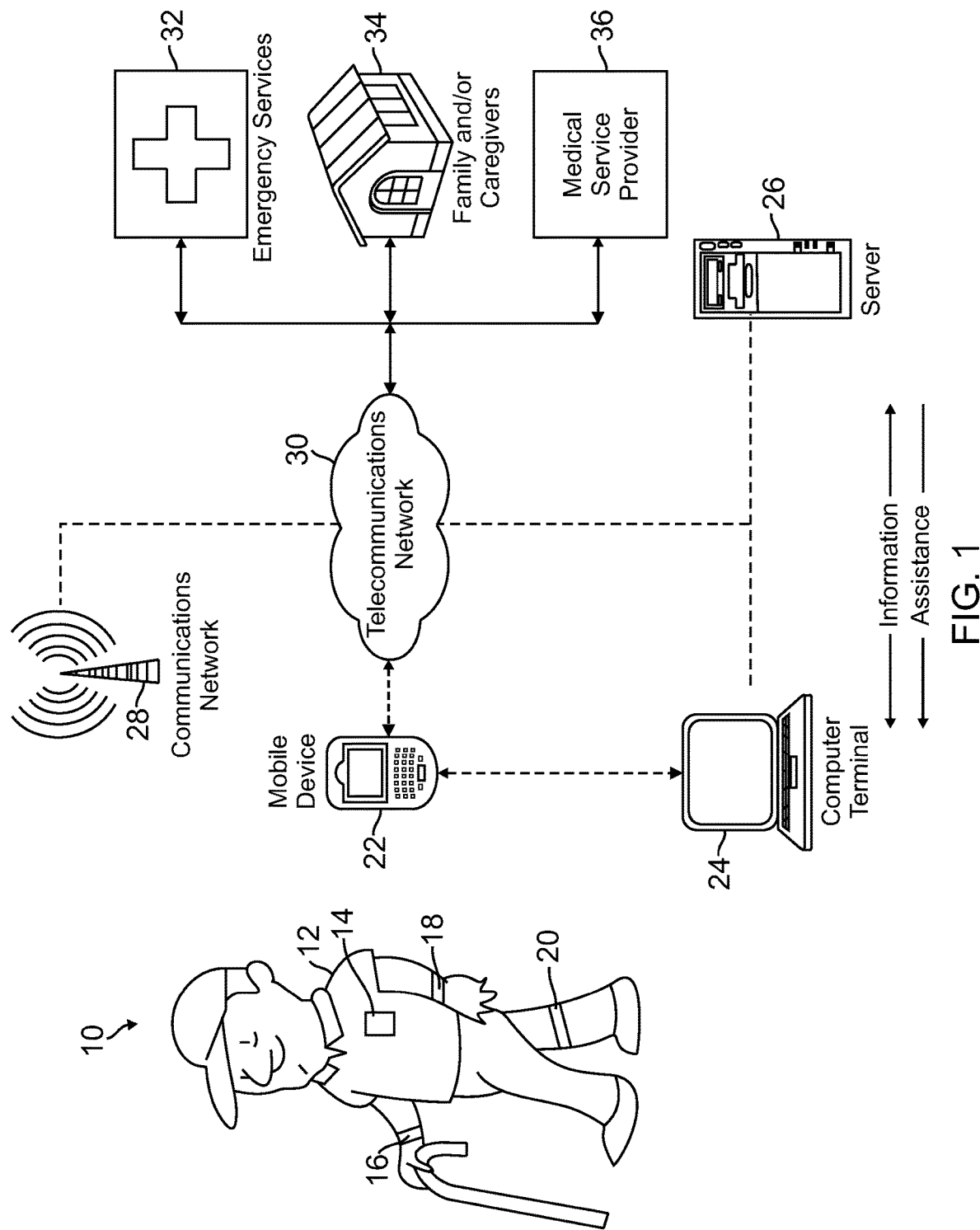
FIG. 1 illustrates a remote health monitoring system according to an embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention may involve using one or more portable computer devices. The term "portable device" is used herein to include any type of electronic device, including those identified above as examples or portable devices with which the method can be used.

The present invention relates generally to a method of detecting and/or predicting seizures by analyzing motor movements in a person and other available data collected from the person or the environment, such as location, movement history, time of day, day of the week, gender, barometric pressure, and the like. The present invention also relates to methods and apparatus for monitoring persons suffering from (or believed to be suffering from) epilepsy, Parkinson's disease, traumatic brain injury, tremors, narcolepsy, or the like diseases and conditions, as well as conditions such as sleep apnea.

Although the present invention is described herein for use regarding seizures, the detection, prediction, analytical, and other methods described herein may be used in other situations, such as heart monitoring, blood sugar monitoring, or other beneficial uses.

In general, the invention may be a method using mobile devices (e.g., mobile phone, tablet computer) equipped to detect motion using accelerometers, gyroscopes, and the like to measure movement in various directions, such as the X, Y, and Z directions. Other coordinate schemes may be used, such as polar coordinates and other appropriate schemes. The method can distinguish abnormal behavior from normal movements.

The invention may also detect "drop seizures" wherein a person drops to the ground without trembling first. The invention may serve to store, tabulate, and compare motion data to improve and update the algorithm and to provide data to medical personnel. The invention may also enable a method of alerting emergency response from third parties. Alerts may be audio, visual, textual, or provided in any other suitable form. Apparatus may be connected to sensors on the body or merely located on or near the body without a direct connection between the body and the mobile device. Also, communication between sensors, modules, the mobile device, and other devices may occur wirelessly.

The invention may include an algorithm for analyzing the measured motion data, comparing characteristics of the specific type of motion by the person to the measured motion data, and determining whether an alert should be sent based on the comparing. Any algorithm in the present invention may be stored on a mobile device located on a remote server and applied to data coming from the mobile device; or stored and accessed at any suitable location. A specific type of motion may include a shake having a sudden to-and-fro movement.

During a seizure the muscles are much more stimulated than under normal circumstances. One burst of epileptic activity can cause a sudden jerk of a limb.

Electromyography (EMG) is a process of graphically recording electrical activity of a muscle during the contraction of a skeletal muscle. Through the EMG, an abnormality in the muscle can be determined by measuring the electrical activity of the skeletal muscle. There are two types of the EMG: needle EMG (nEMG) and surface EMG (s-emg), nEMG uses a needle which is inserted and guided within a muscle tissue to measure muscle action potential during a stable state or an active state. Meanwhile, s-emg uses electrodes attached on the skin. Thus, s-emg is non-invasive and painless.

The s-emg sensors may be arranged to detect electrical activity from muscles using conductive pads placed on the skin of a user. When a muscle beneath a conductive pad is at rest, there is a baseline signal. When a muscle contracts voluntarily, that is, ordinarily, using the muscle to achieve movement or other physical activity, the sensor's signal changes to a certain range of amplitudes and frequencies. However, when the muscle is subject to involuntary activity, such as when the body is experiencing a seizure, the signal produced by the sensor will have a different pattern or range. The sensor may monitor both the amplitude and frequency of the electrical signal within the muscle.

A monitoring sensor having at least one conductive pad or sensor may be arranged to be placed on a respective limb of the body of the user 12 at a monitoring location for sensing and monitoring, over a prolonged period of time, signals at the monitoring location. The monitoring sensor may comprise one or more of an electrodermal activity (EDA) sensor, heart rate sensor, heart rate variability sensor, temperature sensor, and/or a motion sensor. Sensors may be situated near the user 12, such as in a purse, on a car seat, in a clothing pocket, on a pillow or bed next to the user 12, or at any convenient location. Related algorithms may be adjusted to increase sensitivity if detecting user data at an increased distance, such as when detecting movement.

When sensors of muscle movement are employed, these sensors may be on a primary embracing attachment intended to have a fight fit around a part of the body (such as around a part of an arm or around a part of a leg, such as around the wrist of an arm or at the ankle). Each such primary embracing attachment may be provided with one or more sensors for monitoring movement of the respective part of the body, and may include means for communicating a signal (such as a transceiver) and comparison of the signal to a reference signal from at least one reference sensor on another part of the body, a transceiver may be used for communication between the portable device 14,16,18,20 and/or mobile device 22 and a communications network 28.

An accelerometer and/or gyroscope unit may be used for measuring motion data. Data may be collected from tracking motion such as those that may be collected through accelerometer readings. A barometer may be used to detect sudden changes in atmospheric pressure, relating to height (such as if a fall occurs).

Accumulated sweat may interfere with sensor readings. Using a medical adhesive, such as Kryolan (Kryolan Corp., San Francisco, Calif., U.S.) applied directly to the skin may be helpful in avoiding the effect of sweat accumulation on signal amplitude and mean frequency regarding s-emg signals.

Physiological information may include electrodermal activity (EDA), also known as skin conductance or galvanic skin response (GSR). Physiological information may also include skin temperature, heart rate, heart rate variability, and other aspects of a person's condition. An EDA detection hardware may implement an exosomatic measurement of EDA, such that a small voltage is applied to the skin of the user and the resulting potential drop is measured. The EDA detection sensors may measure skin conductance, or the ease with which electrical current can pass through the skin. Skin conductance changes for a variety of reasons primarily connected to how much the user is sweating.

Often, skin conductance spikes before and during a seizure. The severity of a seizure is not necessarily dependent upon the seizure duration, but depends more on how rapidly the brain recovers after the seizure. Fatal seizures are associated with suppressed brainwave activity that lingers after the seizure ends. If the person's brain does not return to normal promptly, the situation may quickly turn for the worse. Injury or death can also occur (to the patient and others nearby) from falls or failure to safely operate motorized vehicles, such as cases where a patient might be driving a car with purportedly controlled seizures, but the effect of seizure suppression medications becomes impaired by other medications.

There is a correlation between the duration of post-seizure brainwave suppression and the incidence of sudden unexplained death in epilepsy (SUDEP), a condition that claims thousands of lives each year in the United States alone.

The higher the skin conductance during a seizure, the longer time needed for the brain to recover. In fact, high skin conductance is linked to deadly seizures. Thus, using the present invention to measure skin conductance and transmit the data to health care providers can help to alert to a deadly seizure needing immediate critical care, or even predict such deadly seizures. Seizures may be predicted due to analyzing present user conditions and comparing to collected data (general and specific) and inputs from environmental conditions.

In general, the present invention provides a method and apparatus which can permit monitoring of epileptic and other seizures, not only when the person is relatively passive (standing, seated, or lying down) but also when the person is subjected to movement either as a result of physical activity or as a result of the person travelling in a vehicle or the like. The present invention may be used to monitor several body movements, such as movements correlating to unintended movements associated with diseases or other malfunctions of the motor apparatus of a person. Although different types of seizure may be very different in their nature; the method and apparatus according to the present invention may be used to monitor multiple types of seizures. In further embodiments, the method and apparatus according to the invention may be used to monitor unintended lack of movement, for example in the case of monitoring for sleep apnea or the like.

Referring now to the drawings in detail, wherein like reference characters refer to like elements, there is shown in FIG. 1 a plan diagram of a remote health monitoring system 10 based on wearable sensors. A patient 12 (also known as a "person" or a "user") may wear portable devices, such as portable device 14 generally worn on the user's body, portable devices 16, 18, which may be worn on a limb, such as at the respective wrists or palms of the user's arms, and portable device 20, which may be worn on a leg. An attachment apparatus for attaching a portable device 14,16, 18,20 to a person may be used, such as an attachment apparatus selected from a group consisting of a strap, cable, string, band, and leash or any other suitable implement to attach a portable device to a user.

Using two portable devices at each limb may be useful as left-right differences on both wrists or both palms may result from a variety of circuits on both sides of the user's brain are involved in eliciting electrodermal activity, including for example, the left amygdala and the right amygdala, each innervating the left and right sides of the electrodermal response. Additionally, the left and right hemispheres of the brain may be differentially activated in some conditions such as depression and anxiety. When portions of the brain have differential activation, skin conductance on the left and right sides may also be differentially activated.

The portable device(s) 14, 16, 18, 20 may optionally be in communication with a mobile device 22, such as a mobile telephone, personal digital assistant (PDA), portable video/music player, electronic book, electronic book reader, tablet computer, portable gaming device, and the like. Communication between the portable device(s) and elsewhere may be established with a computer terminal 24, server 26, communications network 28, and/or a telecommunications network 30 (such as an intranet or the Internet). The various communication means may interact with the server 26. Communications may be directed to and from emergency services 32 (such as public safety emergency centers, fire department, ambulance, paramedics, private security companies, and the like), family members, and/or caregivers 34, and/or medical service providers (such as physicians, nurses, and other medical staff) 36.

Figure 2:
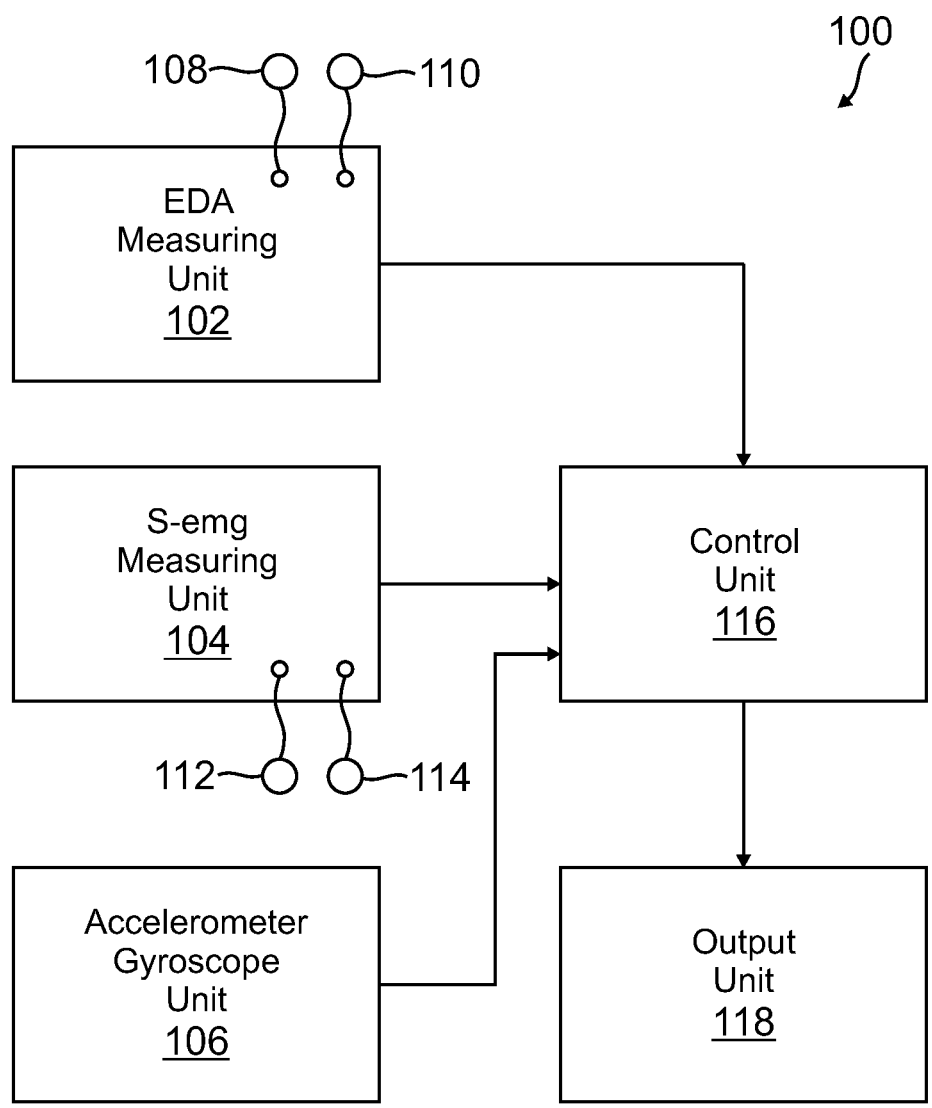
FIG. 2 is a block diagram of an exemplary portable device according to an embodiment of the present invention.

FIG. 2 is a block diagram of an exemplary portable device 100. The portable device 100 includes an EDA measuring unit 102, an electromyogram (s-emg) measuring unit 104, an accelerometer/gyroscope unit 106, a control unit 116, and an output unit 118. The EDA measuring unit 102 may be connected to sensors 108, 110. The s-emg measuring unit 104 may be connected to sensors 112, 114.

Figure 3:
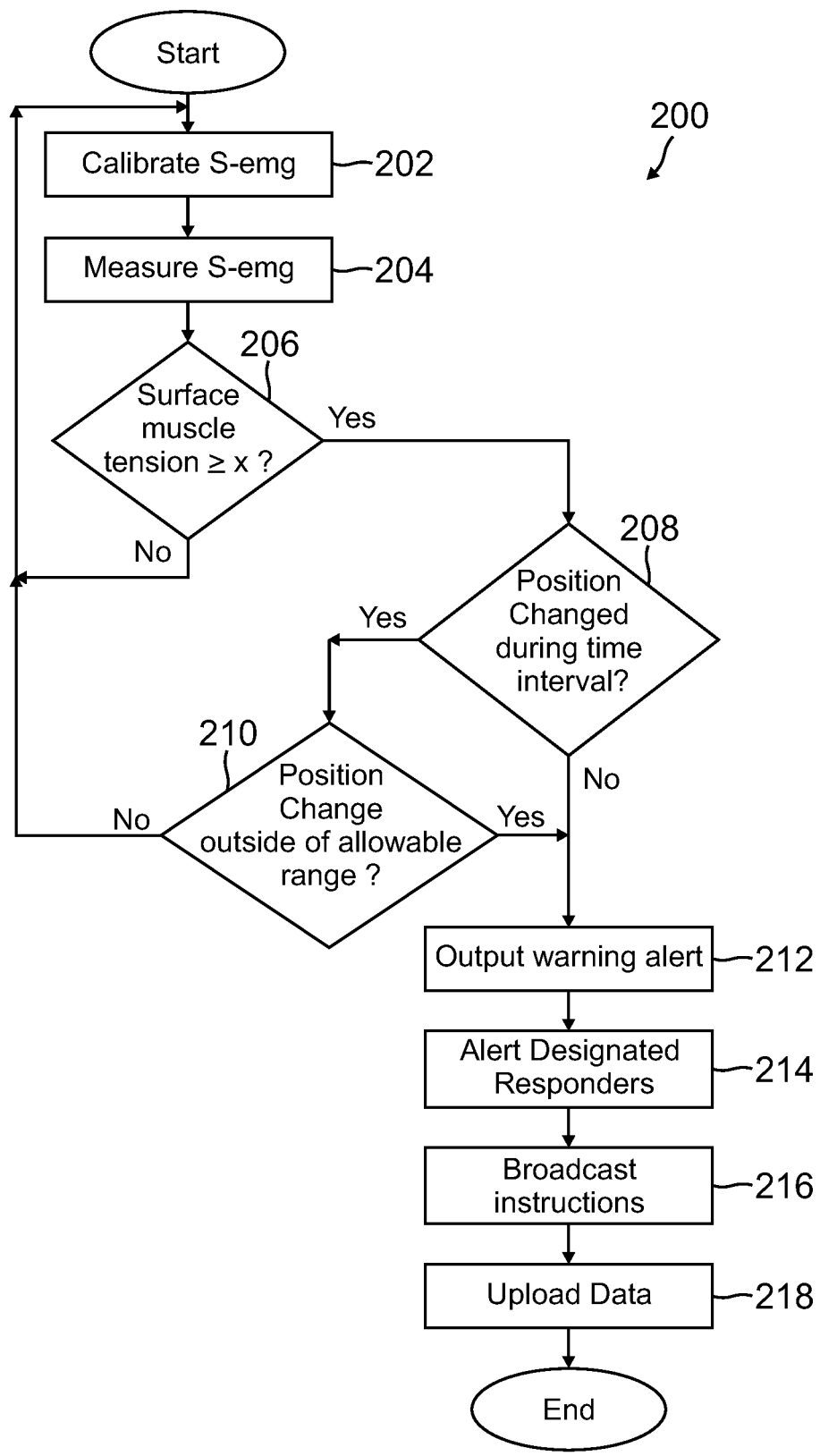
FIG. 3 is a flowchart illustrating a movement detection method according to another embodiment of the present invention.

Referring to FIG. 3, which is a flowchart of a method 200 for abnormal motion detection, operation of the abnormal motion detection apparatus will now be described with reference to FIGS. 1 through 3. Although s-emg is described below, the present invention is not limited to s-emg. In step 202, the measuring units, such as the EDA measuring unit 102 and the s-emg measuring unit 104 may be calibrated to characteristics to the user 12 to normalize detected values. In step 204 the electromyogram measuring unit 104 may periodically measure a muscle tension through two measuring sensors 112 and 114.

According to steps 206, 208, and 210, if the muscle tension value output from the electromyogram measuring unit 104 is greater than a predetermined value and there is not a change in body position for a predetermined time period, for example 30 minutes, as measured by the electromyogram measuring unit 104, the control unit 116 and/or output unit 118 give a warning instructing the user to change his or her current body position.

Further, according to operations 204, 206, 208, 210 and 212, if it is determined that the muscle tension is greater than a predetermined value x, and there is body position frequency change that increases for the predetermined time interval t, there is an abnormal motion for the predetermined time period, and the subject's new motion is outside the allowable range, the control unit 116 and/or output unit 118 give a warning to the user and/or emergency services 32, caregivers and/or family members 34, and medical service providers 36. If the muscle tension is greater than the predetermined value x and there is body position frequency change for the predetermined time period t, and the user's new movement frequency is within the allowable range, this means that only normal movements occurred. Therefore, the process returns to step 204 of periodically measuring the electromyogram.

The method may yet further comprise monitoring a mobile device for any relevant seizure data, querying a user about seizure status or cause, recording any response to the queries, recording seizure status details to form a user log of historical seizure data, uploading seizure data to server system 400, and scheduling an event for follow up. Querying the user 12 may occur in between sep 206 and step 208 or at any other suitable sequence in the method. If the user 12 does not adequately respond to affirm or negate a seizure, the method may proceed on the basis of a likely seizure. If the user 12 subsequently responds that no seizure has occurred, then the method may proceed to a non-seizure state.

The warning is output to the user from the output unit 118. In step 212, the control unit 116 may give a simple warning through the output unit 118. Step 214 may comprise alerting designated responders, such as emergency services 32, caregivers and/or family members 34, and medical service providers 36. Step 216 may comprise broadcasting instructions, such as providing a patient care instruction to the mobile device 22 or to one of the portable devices 14, 16, 18, 20. For example, the patient care instruction may be information on how the caregiver or nearby people should remain calm and summon help to transport the user to a hospital. The patient care instruction may also provide information as to previous seizures, such as severity of previous seizures, medication prescribed, allergy indications, and the like. Step 218 may comprise uploading data to designated providers, the user 12, and/or an online diary or database.

Figure 4:
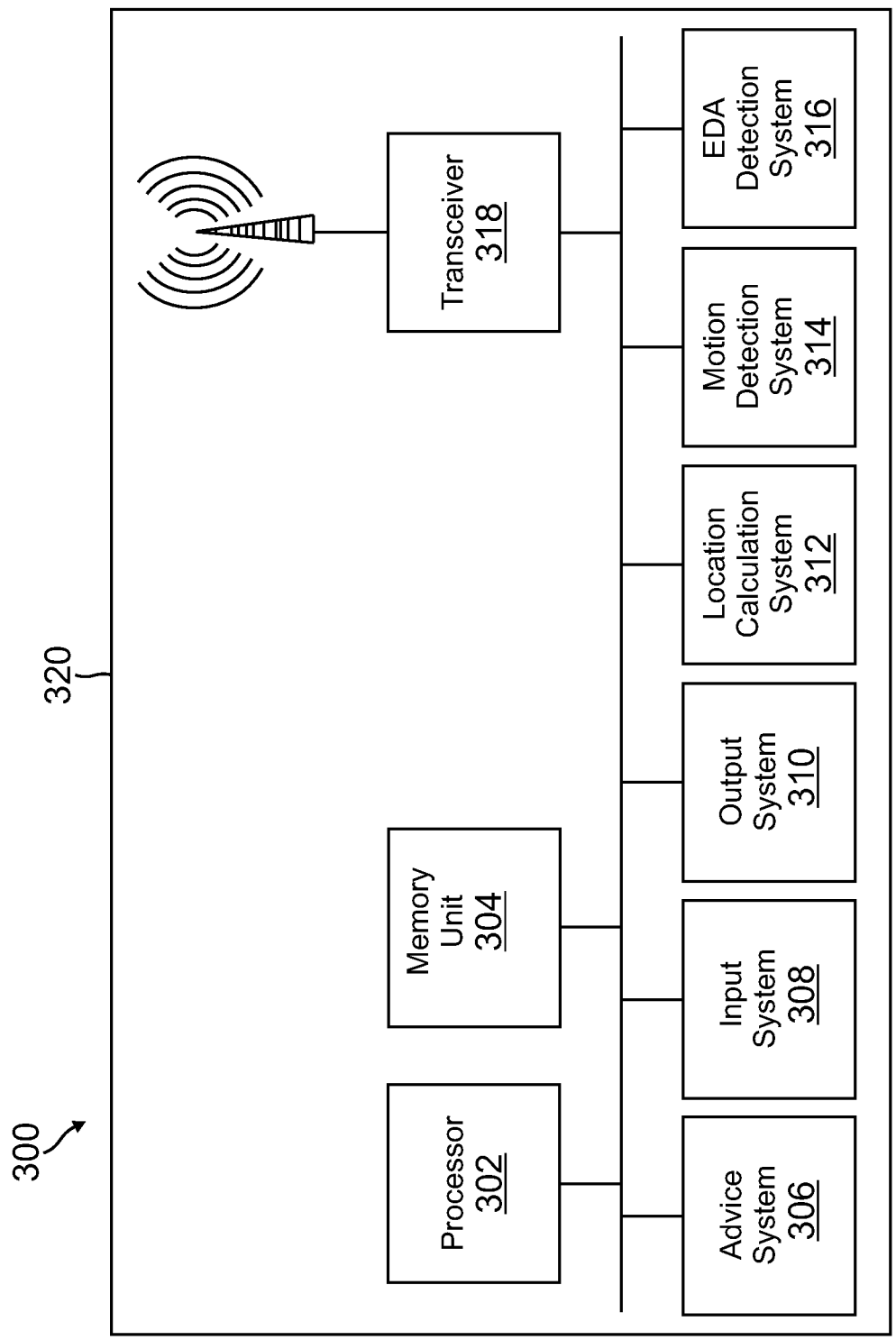
FIG. 4 is a block diagram of system which may be incorporated within the system of FIG. 1.

Referring to FIG. 4, a portable device 300 comprises a processor 302, a memory unit 304, an advice system 306, an input system 308, an output system 310, location calculation system 312, motion detection system 314, EDA detection system 316, and a transceiver 318. "System" in items appearing in FIG. 4 may include hardware and/or software components. In other embodiments, system 300 may include additional components and/or may not include all of the components listed above.

Portable device 300 may be a component of an embodiment of the abnormal motion detection system 10 in which the portable device 300 is contained within a housing 320. The housing 320 may enclose the memory unit 304 and the processor 302. A display may be attached to the housing 320 in a manner for settings so that the specific abnormal motion or a status may be viewed. An input system 308 may be attached to the housing 320 in a manner so that the person 12 or another person may enter settings for the specific type of abnormal motion.

The processor 302 may include any one of, some of, any combination of, or all of multiple parallel processors, a single processor, a system of processors having one or more central processors and/or one or more specialized processors dedicated to specific tasks. Processor 302 may implement an algorithm and generate an indication that a specific abnormal motion may have occurred based on the algorithm, wherein the abnormal motion includes a seizure. Processor 302 may run a program stored on memory unit 304 for detecting seizures, which may be referred to as a seizure detection algorithm. Processor 302 may collect the data from one or more accelerometers, gyroscopes, and/or sensors. Processor 302 may implement a detection and analysis algorithm on the data.

A processor 302 may implement the algorithm to determine whether the motion data retrieved by the motion detector corresponds to the specific type of motion, wherein the specific type of motion is an abnormal motion, including a seizure. The algorithm may be sent to the mobile device 22 from the server 26 and may be tailored to a particular user 12. Processor 302 is optional, because the processor 302 may be located elsewhere.

A memory unit 304 may be used for storing settings for detecting the specific type of motion by the user 12. Memory unit 304 may include, for example, any one of, some of, any combination of, or all of a long term storage system, such as a hard drive; a short term storage system, such as random access memory; a removable storage system, such as a removable drive; and/or flash memory. Memory unit 304 may include one or more machine-readable mediums that may store a variety of different types of information. The term machine-readable medium is used to refer to any medium capable of carrying information that is readable by a machine, excluding signals. One example of a machine-readable medium is a computer-readable medium. Memory unit 304 may store seizure detection engine and/or information about seizures.

The present invention may comprise a memory unit 304 for storage of an algorithm including analyzing motion data, determining whether motion data relates to a specific type of motion has occurred based on the analyzing of motion data, and if it is determined that the specific type of motion has occurred, generating an alert that the specific type of motion occurred, based on the determining. If portable device 300 is a seizure alert system, memory unit 304 is optional, because the processing and storage of seizure information may occur elsewhere.

The motion data may comprise a threshold value for a frequency of oscillation of a body part of the user 12, wherein the analyzing includes comparing a value characterizing the motion to the threshold value, wherein the determining includes determining whether the value surpassed the threshold based on the comparing to determine whether the specific type of motion occurred, and wherein a transceiver summons medical assistance when the value surpasses the threshold.

Advice system 306 may comprise a database of general information for treatment and monitoring of seizures, updated with general information. Advice system 306 may be used to provide general instructions for care of a seizure victim and specific instructions for care of the user based on the motion data associated with the user. Advice system 306 may also comprise a database of specific information specific to the user 12 compiled from medical history, including records of previous seizure events, false positives, false negatives, and the like.

The algorithm downloaded to the mobile device 22 from server 26 may be specifically tailored for a particular user 12—to optimize the accuracy of seizure detection and alerting criteria for that user 12. This patient algorithm could be created by a genetic algorithm or similar method which would create the patient algorithm based on various environmental and status conditions of that user 12 which might increase the probability of correctly predicting, detecting, or alerting of a seizure.

The input system 308 may be used for inputting detected parameters for a specific type of motion by the person 12. Input system 308 may include any one of, some of, any combination of, or all of a keyboard system, a mouse system, a track ball system, a track pad system, buttons on a handheld system, a scanner system, a microphone system, a connection to a sound system, and/or a connection and/or interface system to a computer system, intranet, and/or the Internet (e.g., IrDA, USB), for example. Input system 308 may include a motion detector and/or camera for detecting high frequency motion. Input system 308 or a part of input system 308 may be kept in the possession of a caregiver or in a location easily accessible to a concerned party so that the concerned party may request current motion information and/or past motion and/or seizure information. For example, input system 30$ may include an interface for receiving messages from a PDA or mobile device or may include a PDA and/or mobile device.

Output system 310 may include any one of, some of, any combination of, or all of a monitor system, a handheld display system, a printer system, a speaker system, a connection or interface system to a sound system, an interface system to peripheral devices and/or a connection and/or interface system to a computer system, intranet, and/or the Internet, for example. Output system 310 may include lights, such as a red light and/or a flashing light to indicate a seizure. Output system 310 may include sounds such as beeps, rings, buzzes, sirens, a voice message, and/or other sounds. Output system 310 or a part of output system 310 may be kept in the possession of a caregiver or in a location that will catch a caregiver's attention, such as a PDA, mobile device, and/or a monitor of a computer that is viewed by a caregiver. Output system 310 may send an e-mail, text message, make a telephone call and play a particular message, and/or send other forms of messages to alert a concerned party about the occurrence of a seizure. Output system 310 may be used for providing values of current settings and/or feedback regarding implementation of settings.

Location calculation system 312 may comprise apparatus and software for calculating a user's geographic location or for otherwise determining a location of the user 12, such as GPS, Wi-Fi or other suitable methods. Motion detection system 314 may comprise apparatus and software for detecting movement, such as an accelerometer, gyroscope, and the like. Motion detection system 314 may also comprise a motion detector measuring motion data associated with a user 12. EDA detection system 316 may comprise apparatus and software for detecting skin conductance activity. Transceiver 318 may comprise apparatus for transmitting and receiving electromagnetic signals, such as an antenna.

Figure 5:
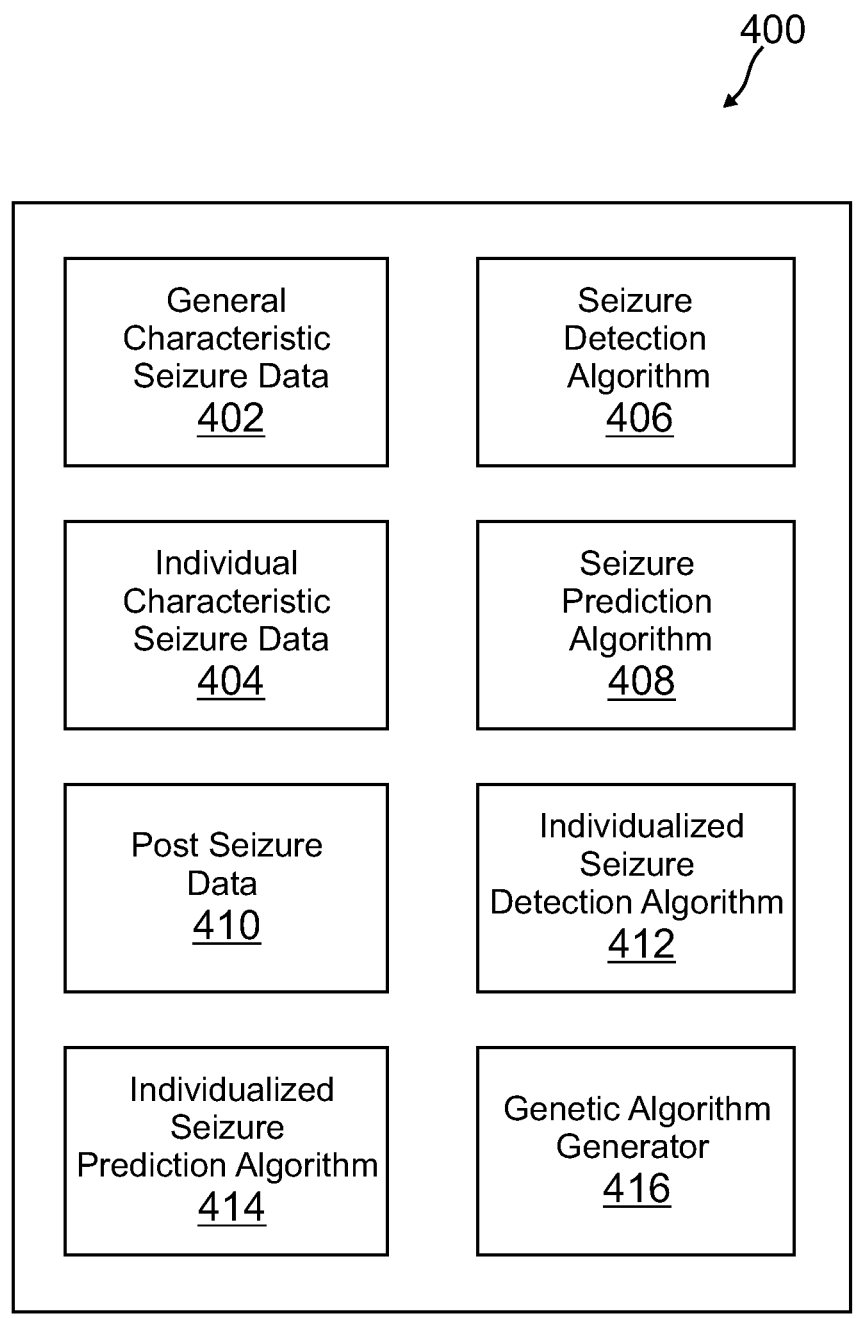
FIG. 5 is a block diagram of an embodiment of a memory unit or server according to an embodiment of the present invention.

FIG. 5 shows a block diagram of an embodiment of server system 400. Server system 400 may include general characteristic seizure data 402, individual characteristic seizure data 404, a genetic algorithm system 416 for periodically creating and updating individualized seizure detection algorithms 406. The genetic algorithm system 416 may also periodically create and download individualized seizure prediction algorithms 408 to each patient's mobile device 22. In other embodiments, server system 400 may include additional components and/or may not include all of the components listed above.

A seizure detection algorithm 406 analyzes seizure data 410 and additional information that may not seem on the surface to be related to seizures, to forecast the likelihood and intensity of seizures for a particular individual and to create an individualized seizure detection algorithm 412 and an individualized seizure prediction algorithm 414 for each particular patient. General characteristic seizure data 402 may include general information characterizing a seizure based on widely available seizure information compiled from the general population. Characteristic seizure data 402 may include thresholds for various parameters that are indicative of a seizure having taken place. For example, characteristic seizure data may include one or more thresholds for the frequency of oscillation of various body parts during a seizure, thresholds for frequency of oscillation of the acceleration or other parameter output by the accelerometer and/or a threshold of the frequency of oscillation of cantilever that is part of an accelerometer that is included within portable device(s), 14,16,18,20 and/or mobile device 22. Characteristic seizure data 402 may include patterns of data that are indicative of a seizure. Characteristic seizure data 402 may include default data that is not specific to any one individual.

Individual characteristic seizure data 404 may include specific information characterizing a seizure based on seizure information compiled from the user 12. Individual characteristic seizure data 404 may include data that is or is not typically associated with predicting or detecting seizures, such as thresholds for various parameters that are indicative of a seizure having taken place, if available, for the individual user 12, or the day of the week, time of day, barometric pressure, and the like, that might correlate with seizure prediction and detection for a particular individual. For example, individual characteristic seizure data 404 may include one or more threshold experiences for the frequency of oscillation of a various body parts of the user 12 during a seizure, thresholds for frequency of oscillation of the acceleration or other parameter output by the accelerometer and/or a threshold of the frequency of oscillation of cantilever that is part of an accelerometer that is included within portable device(s) 14,16,18,20 and/or mobile device 22. Characteristic seizure data 404 may include patterns of data that are indicative of a seizure and/or may include data that is specific to user 12.

Post-seizure data 410 may store information about seizures as the seizures are happening, which may be reviewed further at a later date to better determine the characteristics of the seizures that are specific to user 12 so that abnormal motion detection system 10 may more reliably predict and/or detect the seizures of user 12. Additionally or alternatively, post-seizure data 410 may be used for diagnosing and treating a seizure, including data for a particular individual. In an embodiment, all detection results may be recorded on the hard disk or flash drive of a computer or on an external memory card (SD, Compact Flash, USB drive, and the like). Sometimes, knowledge of whether a seizure occurred may be important to know the effectiveness of a medication or for other medical reasons. However, some patients are unaware of having experienced a seizure, By storing past seizure data 410, user 12 may still be informed that a seizure has occurred. The user may be queried by server system 400 as to what factors they recall just prior to having the seizure. The data may include images, videos, accelerometer. EDA, s-emg, or other sensor data. The data may include plots, summaries and/or other forms of data. The data may also be analyzed and reviewed later by a medical professional for diagnosis, treatment, and/or other medical purposes.

Genetic algorithm generator 416 can serve to adapt algorithms for creating individual algorithms customized to individual characteristics of a user to create, improve, and optimize individual seizure detection algorithm 412 and individualized seizure prediction algorithm 414. The genetic algorithm generator may generate, store, and/or transmit individualized algorithms stored in individual seizure detection algorithm 412 and/or individualized seizure prediction algorithm 414 for users. The individualized algorithms 412, 414 may be downloaded into a portable device 14, 16, 18, 20 or mobile device 22. The system may "learn" about a user for optimizing specific prediction and detection algorithms. A genetic algorithm is a search heuristic that mimics or simulates an evolutionary process. The genetic algorithm generator 416 may generate solutions to optimize detecting and/or predicting seizures or other abnormal motions. A genetic algorithm may comprise a genetic representation of the domain of solutions to detection and/or prediction problems and a fitness function to evaluate the domain of solutions for detection and/or prediction of abnormal motions.

The present invention may be operated with or without a mobile device 22. A method for abnormal motion detection using the mobile device 22 may comprise downloading an algorithm to the mobile device 22 tailored to that user 12, updating the mobile device with the optimal available abnormal motion detection algorithm for that user, periodically activating device sensors in listening mode, keeping device sensors active in the event that abnormal motion characteristic patterns are detected, detecting whether abnormal motion characteristic patterns occur, recording sensor data, uploading sensor data, prompting a user to affirm an occurrence of a seizure, interviewing a user as to their recollection of any events or factors prior to the seizure, alerting the user of an alarm sequence, activating an alarm sequence in the event of no user response or of affirmation of seizure by the use, transmitting a device-initiated alarm to server system 400, which may then transmit appropriate alerts to pre-designated alert recipients, recording seizure details, and transmitting seizure details to server system 400.

Keeping device sensors active in the event that abnormal motion characteristic patterns are detected may be useful to conserve battery life in a portable detector, a mobile device, or other equipment. Battery life may be conserved by periodically activating sensors to check for possible seizure activity. If no characteristic pattern is detected, the sensors may be deactivated (e.g., turned off) or remain activated (e.g., turned on) if a likely seizure or emergency event occurs. The method of abnormal motion detection may further comprise calculating a percentage likelihood or risk of seizure for a particular user, collecting baseline data for the user, and labeling data at various times according to the percentage likelihood or risk of seizure at those times.

The method may yet further comprise monitoring a mobile device for any relevant seizure data, querying a user about seizure status or cause, recording any response to the queries, recording seizure status details to form a user log of historical seizure data, uploading seizure data to server system 400, and scheduling an event for follow up. One option is to upload data to an online diary.

The method also may further comprise capturing electrodermal (EDA) activity readings (e.g., skin conductance) from the skin of the user's body to which sensors are in contact.

In another embodiment of the present invention, a method for abnormal motion detection may comprise obtaining an electromyogram waveform of the user and calculating a muscle tension from the electromyogram waveform, if the muscle tension is greater than or equal to a predetermined value, detecting a body position of the user and determining whether there is a change of the body position (location and/or physical body position) during a predetermined period of time, and if there is a change of the user's body position and the body position of the subject is not within an allowable position change range, outputting an alert. Motion data may be used such that the method may further comprise providing individualized instructions for care of a particular seizure victim and specific instructions for care of the user based on motion data, and various other types of data, associated with the user.

The present invention may involve other features. Instructions selected for transmission through the system may be optimized according to particular characteristics of the user 12. For example, the invention may detect a location for a user 12 and provide instructions tailored to that location. Also, depending upon the location of the user 12, information may need to be provided in a local language based on the geographical location or user preferences. Instructions for events may be updated from time-to-time, such as when medical information changes, for example.

It should be understood, of course, that the foregoing relates to exemplary embodiments of the invention and that modifications may be made without departing from the spirit and scope of the invention as set forth in the following claims. For example, method steps, such as recording, computing, and other steps may be conducted remotely from a mobile device, such as is commonly understood as "cloud computing."

Furthermore, a method described herein may be performed in one or more sequences other than the sequence presented expressly herein.

We claim:

1. A portable device comprising:
   a housing including:
   an accelerometer and/or gyroscope unit for measuring motion data and a body position of a person;
   a memory unit for storing settings for detecting high frequency motion by the person received from the accelerometer and/or gyroscope unit;
   a processor to implement an algorithm and generate an indication whether a specific abnormal motion occurred based on the algorithm, wherein the abnormal motion includes a seizure and the algorithm analyzes the measured motion data, comparing characteristics of the high frequency motion by the person to the measured motion data and body position of the person and determining seizure status and whether an alert should be sent based on the comparing, and further to adapt the algorithm for creating an individual algorithm customized toward characteristics of the high frequency motion by the person and information specific to a user compiled from medical history;
   a monitoring sensor, in electronic communication with the memory unit and processor, having at least one conductive pad arranged to be placed on a respective limb of the body of the person at a monitoring location for sensing and monitoring, over a prolonged period of time, signals from the respective limb of the body of the person and an electromyogram waveform of the user and calculating a muscle tension from the electromyogram waveform; and
   a display for viewing the abnormal motion or a determined seizure status,
   wherein the processor is further configured to
      determine whether the muscle tension is greater than a predetermined value, and whether the muscle tension is greater than the predetermined value,
      determining whether there is a change of the body position of the person during a predetermined period of time, and
      when there is a change of the body position of the person that is not within an allowable position change range, outputting an alert.

2. The portable device of claim 1, further comprising:
   an attachment apparatus for attaching the portable device to the person.

3. The portable device of claim 2, wherein the attachment apparatus is selected from a group consisting of a strap, cable, string, band, and leash.

4. The portable device of claim 1 wherein the monitoring sensor comprises one or more of an electrodermal activity sensor, heart rate sensor, heart rate variability sensor, temperature sensor, and a motion sensor.

5. The portable device of claim 1, further comprising a transceiver for communication between the portable device and a telecommunications network.

6. The portable device of claim 5, wherein the telecommunications network includes one or more of the Internet and an intranet.

7. A method for abnormal motion detection, comprising:
   downloading an optimal available abnormal motion detection algorithm to a mobile device;
   periodically activating device sensors electronically connected with the mobile device, via a processor electronically connected with the mobile device in listening mode;
   keeping device sensors, via the processor, active in the event that abnormal motion characteristic patterns are detected;
   implementing, via the processor, the optimal available abnormal motion detection algorithm;
   detecting, via the device sensors, whether abnormal motion characteristic patterns occur;
   generating an indication, via the processor, whether a specific abnormal
   motion occurred based on the optimal available abnormal motion detection algorithm;
   recording sensor data to a memory unit electronically connected with the mobile device;
   prompting a user of the mobile device to affirm, via an interface for the mobile device, an occurrence of a seizure;
   alerting a user, via an output unit electronically connected with the mobile device, of an alarm sequence;
   providing general instructions for care of the user victim and instructions for care of the user based on the sensor data associated with the user;
   providing specific information specific to the user compiled from medical history;
   activating an alarm sequence, from the mobile device, in the event of no user response, via the interface for the mobile device, or of affirmation of seizure by the user, via the interface for the mobile device;
   transmitting a device-initiated alarm, via a transceiver, in wireless communication with the mobile device, to the server system;
   transmitting an alert from the output unit, to pre-designated alert recipients;
   adapting the optimal available abnormal motion detection algorithm for creating an individual algorithm customized toward characteristics of the user's abnormal motion; and
   storing a predetermined value for the user's muscle tension in the memory unit;
   obtaining an electromyogram waveform of the user, via the processor, and calculating a muscle tension from the electromyogram waveform, via the processor;
   determining whether the muscle tension is greater than or equal to a predetermined value stored in the memory unit;
   detecting a position of the user;
   determining whether there is a change of the position during a predetermined period of time; and when there is a change of the user's position and the position of the subject is not within an allowable position change range,
outputting an alert to the mobile device.

8. The method of claim 7, further comprising:
calculating a percentage likelihood or risk of seizure;
collecting baseline data for the user; and
flagging data according to the percentage likelihood or risk of seizure.

9. The method of claim 8, further comprising:
periodically deactivating the sensors if the percentage likelihood or risk of seizure is below a predetermined percentage for those times.

10. The method of claim 7, further comprising:
monitoring a mobile device for any relevant seizure data;
querying a user about seizure status, via the interface for the mobile device; recording any response to the query to the memory unit electronically connected with the mobile device;
recording seizure status details to the memory unit electronically connected with the mobile device to form a user log of possible prior seizure data;
uploading seizure data to a server; and
scheduling an event and storing the event to the memory unit electronically connected with the mobile device for follow up.

11. The method of claim 7, further comprising:
contacting sensors to the skin of the user's body; and
capturing electrodermal activity readings from the skin of the user's body to which sensors are in contact.

12. The method of claim 7, further comprising:
uploading data to an online diary on the server system.

13. The method of claim 7, further comprising:
providing instructions for care of a seizure victim and specific instructions for care of the user based on motion data associated with the user;
providing the instructions from emergency services to the user via a telecommunications network.

14. The method of claim 7, further comprising:
periodically deactivating the sensors if no characteristic of the user's abnormal motion is detected.

* * * * *